United States Patent [19]

Lysenko

[11] Patent Number: 4,766,244

[45] Date of Patent: Aug. 23, 1988

[54] HIGH PURITY PROCESS FOR THE PREPARATION OF 4,6-DIAMINO-1,3-BENZENEDIOL

[75] Inventor: Zenon Lysenko, Midland, Mich.

[73] Assignee: The Dow Chemical Company, Midland, Mich.

[21] Appl. No.: 925,358

[22] Filed: Oct. 30, 1986

[51] Int. Cl.$^4$ .............................................. C07C 85/11
[52] U.S. Cl. ................... 564/418; 564/443; 568/709; 568/711
[58] Field of Search ................ 564/418, 443; 568/709, 568/711

[56] References Cited

U.S. PATENT DOCUMENTS 4,005,143  1/1977  Bohm et al. ..................... 564/418

FOREIGN PATENT DOCUMENTS 48-27300  8/1973  Japan ................................ 564/418

OTHER PUBLICATIONS

Wolfe, J. F. et al., *Macromolecules*, vol. 14, No. 4, pp. 909–914, (1981).

*Primary Examiner*—Richard L. Raymond
*Assistant Examiner*—John A. Sopp

[57] ABSTRACT

High purity 4,6-dinitro-1,3-benzenediol is prepared by (a) contacting a 1,2,3-trihalobenzene with a nitrating agent and an acid under reaction conditions such that a 1,2,3-trihalo-4,6-dinitrobenzene is produced, (b) contacting the 1,2,3-trihalo-4,6-dinitrobenzene prepared in (a) with an alkanol and a base under reaction conditions such that a 4,6-dinitro-2-halo-1,3-benzenediol is produced, and (c) contacting the 4,6-dinitro-2-halo-1,3-benzenediol prepared in (b) with a hydrogenating agent in the presence of a solvent and a catalyst under reaction conditions such that a 4,6-diamino-1,3-benzenediol is produced. This 4,6-diamino-1,3-benzenediol is useful in the preparation of high molecular weight polybenzoxazoles.

8 Claims, No Drawings

HIGH PURITY PROCESS FOR THE PREPARATION OF 4,6-DIAMINO-1,3-BENZENEDIOL

BACKGROUND OF THE INVENTION

This invention relates to a process for the preparation of 4,6-diamino-1,3-benzenediol. More specifically, it pertains to a high purity multistep synthesis for the preparation of 4,6-diamino-1,3-benzenediol. zenediol.

Diaminobenzenediols are useful as monomers for the preparation of polybenzoxazoles. Polybenzoxazoles can be prepared by reacting diaminodihydroxybenzenes with bisacids, bisacid halides, bisesters or bisnitriles. In order to obtain a high molecular weight polybenzoxazole which can be effectively spun into workable fibers, it is necessary that the starting materials used to form the polybenzoxazoles are of very high purity. Polybenzoxazoles prepared from highly pure diaminobenzenediols can be spun into fibers having high tensile strength and thermal stability. Such fibers are desirable for military, aerospace and other applications requiring high performance materials.

The traditional method for preparing 1,3-diamino-4,6-dihydroxybenzene involves the treatment of diacetyl-1,3-benzenediol with white nitric acid. The treatment with nitric acid results in the formation of the undesirable 2,4,6-trinitro-1,3-benzenediol. Repeated recrystallizations are required to isolate the desired 4,6-dinitro-1,3-benzenediol from the undesirable by-product. The 4,6-dinitro-1,3-benzenediol is catalytically hydrogenated in dilute hydrochloric acid to produce the 4,6-diamino-1,3-benzenediol. See Wolfe et al., *Macromolecules*, 14. p. 909 (1981). This process is disadvantageous in that it requires extensive purification and utilizes expensive starting materials.

What is needed is an economical high yield process which results in the formation of a substantially pure 4,6-diamino-1,3-benzenediol. Such a process would provide for the efficient production of 4,6-diamino-1,3-benzenediols which could be used to form the desirable high molecular weight polybenzoxazoles.

SUMMARY OF THE INVENTION

The present invention is such a process for the preparation of 4,6-diamino-1,3-benzenediol in high purity and yield. The process of the present invention comprises (a) contacting a 1,2,3-trihalobenzene with a nitrating agent and an acid under reaction conditions such that a 1,2,3-trihalo-4,6-dinitrobenzene is produced, (b) contacting the 1,2,3-trihalo-4,6-dinitrobenzene prepared in (a) with an alkanol and a base under reaction conditions such that a 4,6-dinitro-2-halo-1,3-benzenediol is produced, and (c) contacting the 4,6-dinitro-2-halo-1,3-benzenediol prepared in (b) with a hydrogenating agent in the presence of a solvent and a catalyst under reaction conditions such that a 4,6-diamino-1,3-benzenediol is produced.

It has been discovered that the reaction conditions and steps described herein lead to a 4,6-diamino-1,3-benzenediol of unusually high purity which can be utilized to prepare high molecular weight polybenzoxazoles.

DETAILED DESCRIPTION OF THE INVENTION

The first step of the process of the present invention involves contacting a 1,2,3-trihalobenzene with a nitrating agent and an acid. Halo herein refers to chloro, bromo or iodo. Any 1,2,3-trihalobenzene is suitably employed. Examples of such suitable trihalobenzenes include 1,2,3-trichlorobenzene, 1,2,3-tribromobenzene, 1,2,3-triiodobenzene, 1,2-dichloro-3-bromobenzene, 1-chloro-2,3-dibromobenzene, 1-fluoro-2,3-dichlorobenzene, 1,3-dibromo-2-chlorobenzene and other 1,2,3-trihalobenzene isomers. Of these trihalobenzenes, 1,2,3-trichlorobenzene is most preferred.

Any nitrating agent which will nitrate the 1,2,3-trihalobenzene at the 4 and 6 positions under the reaction conditions described herein can be utilized in the first step of the present invention. Suitable nitrating agents include alkali metal nitrates such as sodium and potassium nitrate and nitric acid at various concentrations, such as fuming nitric acid and concentrated nitric acid. Concentrated nitric acid, e.g., from about 60 to about 75 weight percent nitric acid, especially about 70 weight percent, is the most preferred nitrating agent.

Any acid which, in the presence of nitric acid, will facilitate the formation of nitronium ions under the reaction conditions described herein can be utilized in the first step of the present process. Suitable acids for this purpose include trifluoroacetic acid, hydrochloric acid and sulfuric acid, with hydrochloric acid being preferred and sulfuric acid being most preferred.

Suitable molar ratios of nitrating agent to trihalobenzene are those sufficient to cause the substitution of 2 nitro groups on the benzene ring at the proportion of 2 nitro groups per molecule of trihalobenzene. Examples of such ratios are those in the range from about 2:1 to about 3.3:1, with about 2.1:1 to about 2.5:1 being preferred. The most preferred ratio is 2.2:1. Typical molar ratios of acid, preferably sulfuric acid, to trihalobenzene are in the range from about 10:1 to about 20:1, with about 11:1 to about 15:1 being preferred. The most preferred ratio is 11.3:1.

The temperature of the first step can be any temperature at which nitration will occur. Typical temperatures are in the range from about −5° C. to about 135° C., with from about 15° C. to about 80° C. being preferred. The pressure of the first step can be any pressure at which nitration will occur. Preferred pressures are about atmospheric, although subatmospheric or superatmospheric pressures can be employed.

The 1,2,3-trihalo-4,6-dinitrobenzene produced by the first step can be isolated by conventional precipitation and filtration techniques and is typically obtained in greater than about 95 percent purity, preferably greater than 98 percent purity and most preferably greater than about 99.9 percent purity. The product of the first step is typically obtained in yields greater than about 95 percent, preferably greater than about 97 percent and most preferably greater than about 98.9 percent. The 1,2,3-trihalo-4,6-dinitrobenzene can be immediately utilized in the second step of the present invention without further purification.

The second step of the present process involves contacting the 1,2,3-trihalo-4,6-dinitrobenzene prepared in the first step with an alkanol and a base. Any alkanol which will deprotonate in the presence of base can be used in the second step of the present process. Suitable alkanols include lower alkanols such as methanol, ethanol and propanol, with ethanol being preferred. Methanol is the most preferred alkanol. Any base which will generate hydroxide ion can be used in the second step of the present process. Suitable bases include alkali metal hydroxides such as sodium and potassium hydroxide or alkali metal alkoxides such as sodium ethoxide. Preferred bases are sodium hydroxide and potassium hydroxide, with sodium hydroxide being most preferred.

Suitable molar ratios of alkanol to the trihalodinitrobenzene are those sufficient to displace at least one of the halogens with alkoxide. Examples of such suitable ratios are those in the range from about 1:1 to about 20:1, with about 1:1 to about 15:1 being preferred. The most preferred ratio is 10:1. Suitable molar ratios of base to trihalodinitrobenzene are those sufficient to neutralize all acidic species in the reaction mixture and to effect displacement of halogens on the aromatic ring. Examples of such suitable ratios are those in the range from about 7:1 to about 1:1, with about 6:1 to about 1:1 being preferred. The most preferred ratio is 5.5:1.

The temperature of the second step can be any temperature at which displacement of halogen will occur. Suitable temperatures are in the range from about 0° C. to about 150° C., with from about 25° C. to about 85° C. being preferred. The pressure of the second step can be any pressure at which displacement of halogen will occur. Preferred pressures are generally about atmospheric, although subatmospheric and superatmospheric pressures can be suitably employed.

The 4,6-dinitro-2-halo-1,3-benzenediol produced by the second step can be isolated by conventional precipitation and filtration techniques and is typically obtained in greater than about 90 weight percent purity, preferably greater than 95 weight percent purity and most preferably greater than about 99.9 weight percent purity. The product of the first step is typically obtained in yields greater than about 80 mole percent, preferably greater than about 88 mole percent and most preferably greater than about 97 mole percent based on moles of 1,2,3-trihalobenzene charged into the reaction. The 4,6-dinitro-2-halo-1,3-benzenediol can be utilized as is in the third step of the present invention. Alternatively it may be purified further by recrystallization from a suitable solvent such as methanol.

The third step of the present invention involves contacting the 4,6-dinitro-2-halo-1,3-benzenediol produced in the second step with a hydrogenating agent in the presence of a solvent and a catalyst. The hydrogenating agent can be any material which will supply hydrogen to the reaction. Suitable hydrogenating agents include hydride reducing agents such as lithium aluminum hydride, dissolving metal reducing agents such as zinc metal and amalgoms of sodium or cadmium, for example, and hydrogen gas. Of the hydrogenating agents, hydrogen gas is the most preferred.

The solvent which is optionally employed in the third step can be any solvent which will remain inert under the hydrogenation conditions. Suitable solvents include alcohols such as ethanol, methanol and propanol, as well as alkylene glycols such as ethylene glycol and carboxylic acid such as acetic acid, with carboxylic acid being preferred. The most preferred solvent is acetic acid.

The hydrogenation catalyst can be any material which contains a noble metal and will catalyze the reduction of the nitro groups of and the elimination of the halogen from the 4,6-dinitro-2-halo-1,3-benzenediol. Examples of suitable catalysts include noble metals on carbon, noble metal oxides and noble metals supported on alkaline earth carbonates. Noble metals herein refer to gold, silver, platinum, palladium, iridium, rhodium, mercury, ruthenium and osmium. Preferred catalysts include palladium-on-carbon, platinum-on-carbon and platinum oxide. The most preferred hydrogenation catalyst is 10 weight percent palladium-on-carbon. Preferred catalysts are those sold commercially as hydrogenation catalysts for the reduction or elimination of halogen from an aromatic.

The catalyst is employed in an amount which is sufficient to catalyze the conversion of starting material in the presence of a hydrogenating agent to the corresponding diaminobenzenediol. Typically, from about 0.001 to about 1 molar equivalents of catalyst are present per equivalent of dinitrohalobenzenediol. Preferably, from about 0.01 to about 0.5 and most preferably from about 0.01 to about 0.1 equivalents of catalyst are present throughout the reaction.

Suitable concentrations of dinitrohalobenzenediol in the reaction medium are those sufficient to afford an efficient recovery of product. Examples of such suitable concentrations are those in the range from about 0.001 to about 10 molar, with from about 0.1 to about 2 M being preferred. The most preferred concentration is 1 M.

The amount of hydrogenating agent employed in the third step is suitably an amount sufficient to convert all nitro moieties to amino moieties and to remove the halo moiety from the dinitrohalobenzenediol. Examples of such suitable amounts include those in the range from about 700 to about 2000 mole percent based on moles of dinitrohalobenzenediol, preferably from about 710 to about 750 mole percent. The temperature employed in the third step is sufficient to effect completion of the hydrogenation reaction. Preferably, the temperature is in the range from about 0° C. to about 150° C., most preferably from about 30° C. to about 75° C. Pressures employed are suitably from about 1000 psi to about 1 psi, most preferably from about 400 psi to about 2 psi.

The 4,6-diamino-1,3-benzenediol can be recovered using known recovery methods such as precipitation and filtration. The product is generally isolated and stored as a hydrohalide salt in order to prevent oxidative decomposition. It is also suitable common practice to isolate the product as a salt of any mineral acid such as sulfuric, nitric or phosphoric acid. The 4,6-diamino-1,3-benzenediol of the present invention is typically obtained in a purity greater than 98 weight percent, preferably greater than 99 weight percent, most preferably greater than 99.9 weight percent, with yields being typically greater than 80 mole percent, preferably greater than 85 mole percent and most preferably greater than 95 mole percent, based on moles of 4,6-dinitro-2-halo-1,3-benzenediol charged to the reaction.

SPECIFIC EMBODIMENTS

The following example is given to illustrate the invention and should not be construed as limiting the scope. All parts and percentages are by weight unless otherwise indicated.

EXAMPLE b 1

A. Dinitration of 1,2,3-Trichlorobenzene

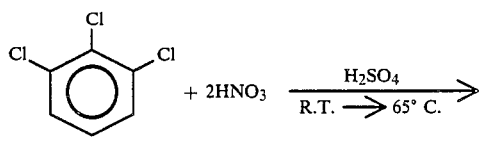

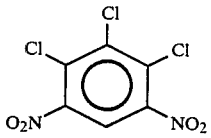

To a 5-liter, 3-necked, round-bottomed flask equipped with a mechanical stirrer, condenser and addition funnel, is added 544.4 g of 1,2,3-trichlorobenzene and 3,425 g of 96.5 percent $H_2SO_4$. The reactor is placed in a variable temperature bath and allowed to warm to 65° C. During this time, 594.1 g of 71 percent concentrated $HNO_3$ is added dropwise at such a rate as to maintain the temperature of the reaction at 65° C. Upon completion of the addition, the reaction mixture is maintained at 65° C. until 98 to 99 percent conversion to dinitrotrichlorobenzene is observed by gas chromatography (usually 1–3 hours) (gas chromatograph conditions: approximately 25M DB-5 capillary gas chromatograph column, oven temp.: 100° C.–250° C., F. To D. Detector, Program rate 20° C./min.). Upon completion of the reaction, 237.1 g of $H_2O$ is added dropwise to the reaction at such a rate as to maintain the temperature of the reaction between 45° C. to 65° C. Vigorous stirring ($\leq$300 rpm) is maintained throughout the course of the reaction. The reaction mixture is subsequently cooled to room temperature and the product is isolated by filtration, washed with 2.2 liters of $H_2$ and air dried to yield 773.5 g of essentially pure 1,2,3-trichloro-4,6-dinitrobenzene (~95 percent isolated yield) (yields usually range from 93 percent to 98 percent). This material is used without further purification.

B. 1,3-Dihydroxy-2-chloro-4,6-dinitrobenzene

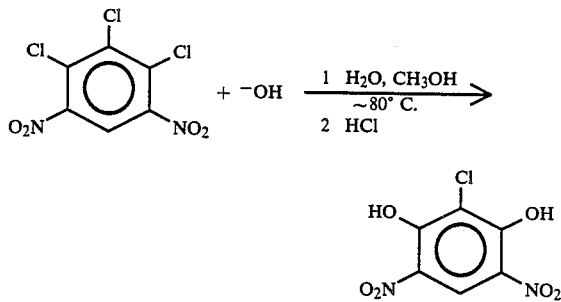

A 5-liter, 4-necked round-bottomed flask is charged with 200.3 g of 1,2,3-trichloro-4,6-dinitrobenzene (0.74 mole), 258.0 g of $CH_3H$ and 717.1 g of $H_2O$. The reaction mixture is stirred at room temperature and 358.4 g of 50 percent NaOH is added in one portion. A slight exotherm is observed and the contents of the reaction are heated to 80° C. When the temperature of the reaction reaches 75° C., the contents of the reactor become homogeneous and another exotherm is observed, concomitant with vigorous reflux, and the temperature of the dark red solution reaches 85° C. Upon completion of this phenomenon, the disodium salt of the product precipitates from the solution. Heating is maintained at 75° C.–80° C. until complete conversion is observed by liquid chromatography (Conditions: 2 cm RP-2 guard column, 15 cm Zorbax phenyl column, & 25 cm Whatman SCX, strong cation-exchange column solvent 30 percent acetonitrile water at 0.02 M $KH_2PO_4$ buffered to pH 2.80 with 85 percent $H_3PO_4$; flow rate 2.0 ml/min. at room temperature. Aliquots from the reaction are neutralized with concentrated HCl diluted with $H_2$ and dissolved with $CH_3CN$) (conversion usually 99.6 to 99.8 percent).

Upon completion, the reaction mixture (a thick slurry) is cooled to room temperature and neutralized with 331.3 g of concentrated HCl (~35 percent). Care is taken to maintain the temperature below 40° C. during the addition of HCl. The resultant slurry is then extracted with 1772.4 g of ethyl acetate. The solvent is concentrated in vacuo and the resulting residue is washed with 104 g of methanol and the product is isolated by filtration and air dried to yield 157.0 g of 1,3-dihydroxy-2-chloro-4,6-dinitrobenzene (90.8 percent isolated yield) assay at 99.886 percent purity as determined by liquid chromatography.

C. Preparation of Diamino Resorcinol Dihydrochloride

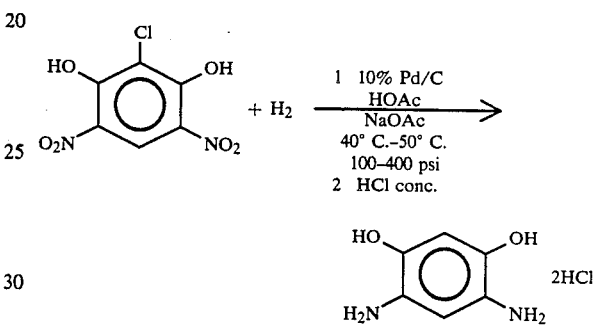

A one-liter Hastalloy C autoclave equipped with a gas dispersion stirrer and cooling coil is charged with 117.3 g (0.5 mole) of 1,3-dihydroxy-2-chloro-4,6-dinitrobenzene, 400 ml of glacial acetic acid, 41 g (~0.5 mole) of NaOAc, ~7.0 g of 10 percent Pd/C and 100 ml of $H_2O$. The sealed reactor is charged with 400 psi of $H_2$ and the temperature is brought to 40° C. and maintained between 40°C.–50° C. during the course of the reaction. After a brief induction period, the uptake of hydrogen becomes extremely rapid and $H_2$ pressure is maintained between 100–400 psi during the reaction. Upon completion, no further uptake of $H_2$ is observed. The reactor is cooled to room temperature, opened and 400 ml of concentrated HCl containing ~10 g of $SnCl_2.2H_2O$ is added to the reaction mixture. The crude product with the catalyst is isolated by filtration. This material is dissolved in 200 g of $H_2O$ at 85° C. and the catalyst is removed by filtration. $H_2O$ (100–300 ml) is added to the filtrate along with 500 ml of HCl and the catalyst-free material is precipitated from the brown solution. Recrystallization may be carried out in the existing solvent or the semi-pure material can be isolated and air dried to afford 100 g of crude diamino resorcinol dihydrochloride, 4,6-diamino-1,3-benzenediol dihydrochloride (96.8 mole percent yield based on the 1,3-dihydroxy-2-chloro-4,6-dinitrobenzene).

D. Recrystallization of Diamino Resorcinol Dihydrochloride (PBO Monomer)

A 100-g portion of PBO monomer is added to 500 g of 3.5M HCl and heated until dissolved. A 10-g portion of decolorizing carbon and 2 to 5 g of $SnCl_2.2H_2O$ are added and refluxing is continued for a period of 15 minutes. The carbon is removed by filtration and the recrystallizing solution is cooled to 0° C. The white needles are isolated by filtration under a $N_2$ blanket and dried to yield 85–95 g of PBO monomer (due to the oxidative instability of this material it is recommended that recrystallization be carried out just prior to polymerization) (85 to 90 percent yield.)

E. Polymerization of 4,6-diamino Resorcinol Bishydrochyloride Derived from 1,2,3-Trichlorobenzene Generally following the procedures outlined in U.S. Pat. No. 4,533,693, a 100-ml resin kettle is loaded with 4,6-diamino resorcinol bishydrochloride (5.00 g, 23.4 mmole), terephthaloyl chloride (4.76 g, 23.4 mmole) and polyphosphoric acid of 77 weight percent $P_2O_5$ (20.0 g). The polymerization is performed under nitrogen with stirring using the following profile: 40° C., 2 hr; 20° C., 120 hr; 40° C., 22 hr: 50° C., 24 hr: +$P_2O_5$ (10.3 g), 95° C., 24 hr 150° C., 24 hr 190° C., 24 hr. The resulting polymer solution exhibited stir-opalescence and readily formed fiber. Inherent viscosity=19.8 dl/g, in 25° C. methane sulfonic acid, c=0.05 g/dl.

What is claimed is:

1. A process for the preparation of 4,6-diamino-1,3-benzenediol in high purity comprising the steps of
   (a) contacting a 1,2,3-trihalobenzene with a nitrating agent and an acid under reaction conditions such that a 1,2,3-trihalo-4,6-dinitrobenzene is produced;
   (b) contacting the 1,2,3-trihalo-4,6-dinitrobenzene with an alkanol and a base under reaction conditions such that a 4,6-dinitro-2-halo-1,3-benzenediol is produced; and
   (c) contacting the 4,6-dinitro-2-halo-1,3-benzenediol with a hydrogenating agent in the presence of a solvent and a catalyst under reaction conditions such that 4,6-diamino-1,3-benzenediol is produced.

2. The process of claim 1 wherein the 1,2,3-trihalobenzene is 1,2,3-trichlorobenzene.

3. The process of claim 2 wherein the nitrating agent is nitric acid, the acid in step (a) is sulfuric acid, the alkanol is methanol, the base is sodium hydroxide, the hydrogenating agent is hydrogen and the catalyst is a palladium-on-carbon hydrogenation catalyst.

4. The process of claim 1 wherein the 4,6-diamino-1,3-benzenediol is recovered in a purity of at least 99 weight percent.

5. The process of claim 1 wherein the 4,6-diaminobenzenediol is recovered in a purity of at least 99.9 weight percent.

6. The process of claim 3 wherein the molar ratio of concentrated nitric acid to the trichlorobenzene is in the range of about 2.1:1 to about 2.5:1, the molar ratio of sulfuric acid to the trichlorobenzene is in the range from about 11:1 to about 15:1 and the temperature in step (a) is in the range from about 15° C. to about 80° C.

7. The process of claim 6 wherein the molar ratio of ethanol to the trichlorodinitrobenzene is in the range from about 1:1 to about 15:1 and the temperature in step (b) is in the range from about 25° C. to about 85° C.

8. The process of claim 7 wherein the mole ratio of hydrogen gas to the 4,6-dinitro-2-chloro-1,3-benzenediol is in the range from about 7 to about 2000, the molar equivalent ratio of the hydrogenation catalyst to 4,6-dinitro-2-chloro-1,3-benzenediol is in the range from about 0.01:1 to about 0.5:1 and the temperature used in step (c) is from about 40° C. to about 50° C.

* * * * *